United States Patent [19]

Detty

[11] Patent Number: 4,963,669
[45] Date of Patent: Oct. 16, 1990

[54] PURIFICATION OF TELLURAPYRYLIUM DYES

[75] Inventor: Michael R. Detty, Rochester, N.Y.

[73] Assignee: Eastman Kodak Company, Rochester, N.Y.

[21] Appl. No.: 371,960

[22] Filed: Jun. 27, 1989

[51] Int. Cl.$^5$ .......................................... C07D 421/06
[52] U.S. Cl. ...................................................... 540/1
[58] Field of Search ............................................. 540/1

[56] References Cited

U.S. PATENT DOCUMENTS

| 4,365,017 | 12/1982 | Detty et al. | 540/1 |
| 4,584,258 | 4/1986 | Detty | 540/1 |
| 4,634,553 | 1/1987 | Detty et al. | 540/1 |

OTHER PUBLICATIONS

Wiberg, Laboratory Technique in Organic Chemistry, p. 99 (1960).

Fishel, Modern Experimental Organic Chemistry, p. 23 (1981).

Detty et al., Tellurapyrylium Dyes, 3, Oxidative Halogen Addition Tellurium Halogen Exchange, Organometallics (1986), 5, pp. 2250-6.

Detty et al., Electron-Accepting Molecules Containing Telluropyranyl Groups. The Effect of Tellurium Oxidation State on Reduction Potentials, J. Org. Chem., 52, 2123 (1987).

Detty et al., J. Org. Chem., 1982, 47, 5235.

Detty et al., Organometallics, (1988), 7, 1131.

Primary Examiner—Robert Gerstl
Attorney, Agent, or Firm—Robert A. Linn

[57] ABSTRACT

Unsymmetrical tellurapyrylium dyes can be ungraded in purity by separating them from symmetrical analogs produced as co-products. The procedure employed for the purification comprises an oxidative halogenation, followed by a fractional crystallization, and a reduction to regenerate the tellurapyrylium dye.

15 Claims, No Drawings

PURIFICATION OF TELLURAPYRYLIUM DYES

FIELD OF THE INVENTION

This invention relates to the separation of a mixture of analogous dyes into two fractions. This invention also relates to the purification or unsymmetrical tellurapyrylium dyes. This invention also relates to a Purification technique that can be used to upgrade a dye product formed by chemical synthesis. In this latter aspect of the invention, an unsymmetrical tellurapyrylium dye is separated from analogous by-products. The separation involves (a) an oxidation reaction to transform a dye molecule into an oxidized derivative, (b) a fractional crystallization based on the relative insolubility of the derivative, and (c) a reduction to recover the dye from the intermediate.

Thus, the separation comprises a combination of physical and chemical steps.

BACKGROUND OF THE INVENTION

Tellurapyrylium dyes are of interest for a variety of electrophotographic, optical recording, and other applications. These dyes can have a variety of substituents, and can be prepared in a number of ways.

A dye having a methine or a trimethine bridge, with a tellurapyrylium nucleus at one end, and a pyrylium, thiapyrylium or selenapyrylium nucleus at the other end of the bridge, will be referred to herein as an "unsymmetrical tellurapyrylium dye," or as "UTPD". Such dyes, with a methine bridge, can be made by reacting a 2- or 4-methyltellurapyrylium nucleus with a chalcogenapyranone. Likewise, unsymmetrical tellurapyrylium dyes (UTPD) with a trimethine bridge can be made by a similar reaction, wherein the chalcogenapyranone is replaced with a chalcogenapyranylacetaldehyde. For these reactions, a solvent of choice is a carboxylic acid anhydride, such as acetic anhydride.

The above-mentioned processes comprise the reaction of an active methyl compound with a carbonyl compound, and can be considered a type of aldol process. The reactions are not straightforward.

The processes generate an olefinic double bond and a molecule of water. The water which is formed leads to process complications. More specifically, water catalyzes a reverse aldol process which leads to the formation of symmetrical dyes, along with the desired unsymmetrical dye. The symmetrical co-products are referred to herein as 'analogs' of the unsymmetrical dye.

By way of illustration, the condensation of 2,6-di-tert-butyl-4-methyltellurapyrylium hexafluorophosphate with 2,6-di-tert-butyl-4-selenapyran-4-one, gives a 95:5 (molar basis) mixture of the tellurapyrylium-4-(selenapyrilidene) methyl dye and the symmetrical selenapyrylium-4-(selenapyrilidene) methyl dye. This is depicted by Equation (1) wherein Me signifies —CH$_3$, and t-Bu signifies tert-butyl.

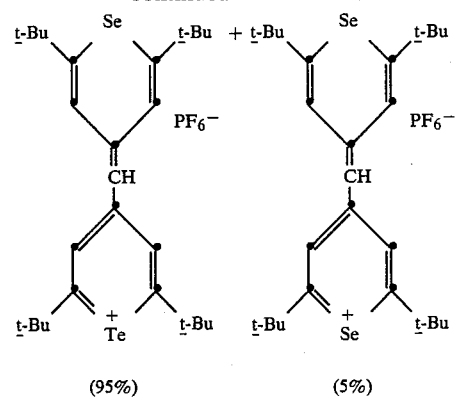

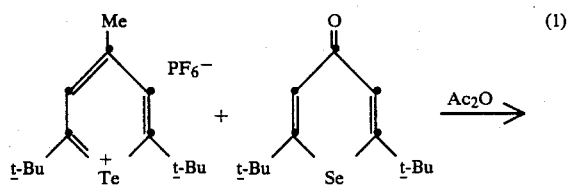

(95%)      (5%)

Similarly, condensation of the same 4-methyl compound with a (chalcogenapyranylidene)acetaldlehyde gives the unsymmetrical trimethine dyes shown in Equation (2):

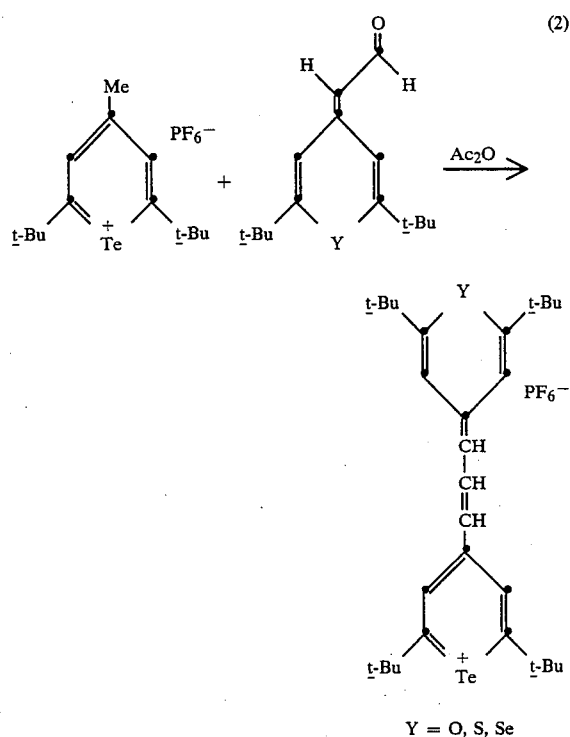

Y = O, S, Se

Reverse aldol reactions also occur during the synthesis of these trimethine bridged compounds. Preparation of the unsymmetrical tellurium/selenium trimethine dye illustrated above using acetic anhydride as a solvent gave a mixture consisting of 92% of the desired dye, 7% of the symmetrical selenium/selenium trimethine dye, and 1% of the symmetrical tellurium/tellurium trimethine dye. Preparation of the unsymmetrical tellurium/sulfur trimethine dye gave a mixture containing 88% of the desired dye and 12% of the symmetrical sulfur/sulfur trimethine dye. Preparation of the unsymmetrical tellurium/oxygen trimethine dye gave a mixture containing 85% of the desired dye and 15% of the symmetrical oxygen/oxygen trimethine dye.

If desired, these dye mixtures can be purified by careful recrystallization or by preparative liquid chromatography. In both cases, purification is tedious and not amenable to large scale purification.

Relative to the lighter halogens, selenium, sulfur, and oxygen, tellurium undergoes a very rapid oxidative addition with halogens. Even tellurapyrylium dyes will undergo oxidative addition of halogens to give tellurium(IV) containing species. These tellurium(IV) containing species are very insoluble relative to the starting tellurapyrylium species.

Thus, this invention provides a purification technique which is simple to carry out a more efficacious or easier to conduct than the previous methods mentioned above. Consequently, this invention is considered to be a significant advance in the art.

RELATED ART

U.S. Pat. No. 4,365,017 discloses tellurapyrylium dyes (also known as telluropyrylium dyes) and their use in increasing the sensitivity of organic photoconductive compositions.

U.S. Pat. No. 4,584,258 discloses such dyes and their use as infrared absorbing dyes in recording elements.

U.S. Pat. No. 4,634,553 discloses 4H-tellurin tellurane sensitizers and their use as election donating photoconductive compositions.

Detty et al, Tellurapyrylium Dyes. 3. Oxidative Halogen Addition Tellurium Halogen Exchange, Organometallics (1986) 5, pp. 2250–6 discloses the oxidative addition of halogens to tellurapyrylium dyes. The reduction of such addition compounds by cyclic voltammetry is also disclosed.

Detty et al, Electron-Accepting Molecules Containing Telluropyranyl Groups. The effect of Tellurium Oxidation State on Reduction Potentials, J. Org. Chem., 52, 2123 (1987) discloses the formation of chlorine, bromine, and iodine oxidative addition products of telluropyranones and their electrochemical reduction.

Detty et al, J. Org. Chem., 1982, 47, 5235 discloses formation of tellurapyrylium dyes.

Detty et al, Organometallics (1988) 7, 1131 also discloses formation of tellurapyrylium dyes.

SUMMARY OF THE INVENTION

This invention relates to a purification technique useful for any tellurapyrylium dye. In a highly preferred embodiment, this invention relates to the purification of unsymmetrical tellurapyrylium dyes having a tellurapyrylium nucleus on one end of a methine-type bridge, and a pyrylium, thiapyrylium or selenapyrylium nucleus on the other end of the bridge.

The purification procedure involves the oxidative addition of a halogen to give a tellurium(IV) containing species. The oxidized species can be selectively crystallized in good yield leaving impurities in solution. After separation of the oxidized species from impurities, it can be reduced to regenerate the tellurapyrylium dye.

DESCRIPTION OF PREFERRED EMBODIMENTS

In a preferred embodiment this invention relates to a process for upgrading the purity of an unsymmetrical tellurapyrylium dye, said dye having a tellurapyrylium nucleus at one end of a methine-type bridge and a pyranyl, thiapyranyl, or selenapyranyl nucleus at the other end of said bridge, by separating said dye from a symmetrical pyrylium, thiapyrylium, selenapyrylium, or tellurapyrylium analog of said dye; said process comprising (i) contacting a mixture of said dye and said analog with a halogen, whereby a tellurium(IV) derivative of said dye is formed, (ii) separating said derivative from the reaction mixture thereby produced by fractional crystallization, and (iii) reducing said derivative with a reducing agent to recover said dye from the Te(IV) derivative.

Tellurapyrylium dyes, also known as telluropyrylium dyes, are described in U.S. Pat. No. 4,365,017. The description of dyes in that patent, Column 1, line 24, to Column 14, line 33, is incorporated by reference herein as if fully set forth. The purification procedure disclosed herein is generally applicable to purification of any dye within the above-referenced disclosure.

In a preferred embodiment, the oxidative addition of halogen is conducted on a mixture of dye materials comprising an unsymmetrical tellurapyrylium dye and one or more symmetrical analogs. Such mixtures can be made by the synthesis procedures set forth in Applicant's previous publication, e.g., J. Org. Chem. (1982) 47, 5235; supra, and Organometallics (1988) 7, 1131; supra, or any similar technique.

In a highly preferred embodiment, the purification process of this invention is conducted to upgrade the purity of an unsymmetrical tellurapyrylium dye having the formula:

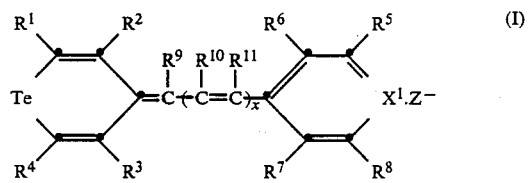

wherein $R^1$, $R^4$, $R^5$, and $R^8$ are selected from the class consisting of hydrogen, alkyl, aryl, and heterocycylic groups having from 1 to about 12 carbon atoms; $R^2$, $R^3$, $R^6$, and $R^7$ are selected from the class consisting of hydrogen, hydroxy, halogen, amino, alkyl groups which contain from 1 to about 12 carbon atoms, aryl groups which contain from 6 to about 12 carbon atoms, and substituents which contain such an alkyl or aryl group, said substituents being selected from alkylthio, arylthio, alkylseleno, arylseleno, and —$NR^{12}R^{13}$ wherein at least one of $R^{12}$ and $R^{13}$ is selected from such alkyl and aryl groups; $R^9$, $R^{10}$, and $R^{11}$ are selected from alkyl groups of 1 to about 12 carbon atoms, halogen, cyano, alkoxy of 1 to about 12 carbon atoms and the like; n is equal to 0, 1, or 2, and $X^1$ is selected from oxygen, sulfur, or selenium.

In the process of the invention, an unsymmetrical tellurapyrylium dye having formula (I) is separated from a symmetrical analog having the formula:

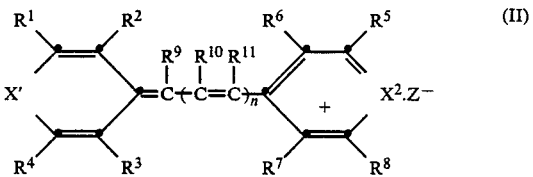

In formula II, the various groups represented by R and n have the same significance as above, and $X^1$ and $X^2$ are the same and selected from the group consisting of oxygen, sulfur, selenium, and tellurium.

In the dyes of formulas I and II, the anion Z is the same, and selected from any suitable anion. Illustrative but not limiting examples of such anions include chloride, bromide, tribromide, triiodide, mesylate, tetrafluoroborate, perchlorate, and hexafluorophosphate.

When the oxidative halogenation step of the process of this invention is used to separate an unsymmetrical tellurapyrylium dye (UTPD) from symmetrical analog(s) produced as by-product(s) in a synthesis procedure such as described and illustrated above, the substituent groups on the rings within the UTPD, and the substituents on the rings in the by-product analog(s) will generally be the same. The substituents in the desired product and the co-products will also have the same relative position on the rings; confer equation (1).

In the development of this invention, work was primarily directed toward separation of UTPD from mixtures in which the UTPD was the most prevalent dye component. Such mixtures are typical of the product mixtures formed in which the UTPD is the desired product and the analogs are formed as less desired co-products. Thus, the process of this invention was developed primarily to separate UTPD from a mixture of that substance and analog(s) thereof, in which the UTPD is present in at least about 70 mole percent and the analog(s) comprise the remainder. The process can be conducted with satisfactory results when the UTPD content is outside this range; for example, from about 50 mole % or greater. However, it is contemplated that the content of the UTPD in the mixture can be much lower, and the process can be conducted, for example, to remove UTPD considered as an undesired impurity in a mixture in which the principal component is a symmetrical product.

The process of this invention comprises the oxidative addition of a halogen to the tellurium in the tellurapyrylium dye. It also involves a fractional crystallization, and a reduction step to recover the tellurapyrylium dye. These steps are discussed in turn, below.

Oxidative Halogenation

In the process of this invention, a solution of dye of formula (I) admixed with one or more analog dyes of formula (II) is contacted with a halogen to oxidize the dye of formula (I) and form a derivative that has the tellurium atom in the tetravalent state. Generally speaking, the amount of halogen employed is sufficient to oxidize all or substantially all of the dye of formula (I), so that it can be separated from the starting mixture. In general, one avoids using too much halogen in order to conserve that reagent, reduce costs, and avoid introducing unnecessary process complications caused by an excess of halogen.

More specifically, the process is conveniently carried out by using an amount of halogen in about equal molar proportion to the amount of tellurium-containing species present in the reaction mixture being treated. A slight excess may be used to assist conversion of all of the dye of formula (I). For example, if a mixture comprises one mole of a dye of formula (I), and one-tenth of a mole of a symmetrical tellurium analog of formula (II), then an operator may select an amount of halogen of from about 1.1 to about 1.2 moles. As apparent to a skilled practitioner, the lower value in this range is equal to the moles of tellurium-containing species in the mixture being treated, and the upper value includes about a 10% halogen excess. A somewhat greater excess can be used if desired. However, it is recommended that less than 1.5 mole equivalents of halogen be employed, per mole of tellurium-containing species. A skilled practitioner can readily determine if too much halogen is being used, since too much halogen excess will cause undesired halogenation or oxidation to take place.

For the oxidative halogenation employed in this invention, it is convenient to admix a solution of the halogen reactant, with a solution of the dye composition used as a starting material. However, the process is not dependent upon this mode of addition, and any other method of intermixing the reaction components which is apparent to a skilled practitioner can be utilized.

As halogen reactants, chlorine and bromine are preferred In many instances, chlorine will be the most preferred reactant because it is cheaper. In other instances, bromine will be preferred, because it is a liquid under ordinary conditions of temperature and pressure, and easier to handle than chlorine. Iodine can be used if desired; however, in many instances its use does not justify the additional cost of this reactant. Furthermore, iodine is a good oxidant, and its use in certain cases can lead to unwanted oxidation. One may use $CF_3OF$, if desired. For the purposes of this invention, that substance is considered a fluorine equivalent. It is also contemplated that other halogenating agents known in the art as equivalent or substantially equivalent to the elemental halogens can be used in the process of the invention. For example, other hypohalides can be employed.

As taught above, the oxidative halogenation is conducted in the presence of an inert organic solvent For the purposes of this invention, an inert solvent is defined as a solvent that does not have a deleterious side effect (on any reactant or product) which occurs to an extent that it cannot be tolerated. In other words, it is not necessary that the solvent be completely inert toward the process ingredients, but only substantially so. Thus, a minor amount of an undesired side reaction can be tolerated, if it does not unduly complicate the process or substantially effect the cost. Halogenated solvents can be efficaciously employed. As a preferred example of a reaction solvent of this type, dichloromethane can be cited. Other solvents which can be used are lower alcohols, aqueous lower alcohols, acetonitrile, and the like. By "lower alcohols" is meant an alcohol having from one to about four carbon atoms.

To conduct the oxidative halogenation, one may use any convenient concentration of reactants. Although the reactants may be present at their saturation limits, one usually uses less concentrated materials. There is no real lower limit on the concentration of the reactants; this is determined from such secondary considerations as the size of the reaction vessel, the cost of the solvent, rates of reaction, and the ease of separation of the halogenated product from the other materials in the next steps of the process. In general, the concentration of the mixture of dyes in the solvent employed is within the range of from about 0.001M to about 1M: more preferably from about 0.1M to about 1.0, and the concentration of the halogen reactant in the solvent employed is from about 0.001M to about 1M: more preferably from about 0.1 to about 1M.

The halogenation reaction proceeds well at mild temperatures. One may conduct the process at ambient temperature, and such temperatures are preferred. If desired, one may use a temperature below or about ambient. The temperature should not be so low as to unduly retard the process, or to introduce process complications caused by reduced solubility of components. A process temperature should be below that temperature at which decomposition of any desired material takes place. A preferred temperature range for the halogenation is from about −78° C. to about 50° C.: more preferably from about 0° C. to about 25° C.

The halogenation proceeds well at ambient pressure; pressures above or below ambient pressure can be used, if desired.

The time required for halogenation is not a completely independent variable, but is dependent at least to some extent on the reactivity of the reactants, the process temperature, and such other secondary considerations. In general, the oxidative halogenation is essentially complete in a few minutes Hence, a typical range of reaction times is from about 0.5 to about 60 minutes, more preferably from about 5 to about 30 minutes.

Fractional Crystallization

After the oxidative halogenation is conducted to product the Te(IV) derivative of the UTPD, the reaction mixture is treated to remove the derivative from solution. A suitable technique is to add a second solvent to the reaction mixture to reduce the solubility of the derivative and precipitate the Te(IV) derivative from solution. Optionally, one can chill the resultant mixture to precipitate additional derivative from the mixture.

As an example, the fractional crystallization used in this invention can be conducted by adding diethyl ether to the mixture formed by the above-described halogenation step. The ether added can be in about an equal volume to the volume of solvent employed in the halogenation. Greater or lesser amounts of solvent can be used, so long as the amount of the added solvent (i) decreases the solubility of the halogenated derivative of the UTPD, without decreasing the solubility of an analog, or derivative thereof, to the extent that the fractional crystallization of the UTPD becomes not an efficient means to separate the UTPD derivative from undesired materials. It is within the skill of the art of a skilled practitioner (familiar with the teachings herein) to determine by routine experimentation the solvent and amount thereof to use, and the extent of chilling to employ to have an efficient separation of the halogenated derivative of the UTPD.

If chilling is employed to aid the fractional crystallization, the temperature employed can be relatively mild, e.g., a temperature within the range of from about 0° to about −10° C. A skilled practitioner will recognize that this temperature range is not critical, and temperatures outside the range can be employed, if desired.

Reduction

After the fractional recrystallization, the halogenated Te(IV) derivative is redissolved in a suitable solvent. For this purpose, one may use a halogenated solvent, lower alcohol, aqueous alcohol, or nitrile such as acetonitrile. When the derivative is in solution, it is more readily contacted with the reducing agent used to regenerate the UTPD. The redissolving of the derivative can be accomplished in any convenient manner apparent to a skilled practitioner.

The reduction of the Te(IV) derivative can be conducted in any convenient manner. For example, it can be carried out using a coulometric procedure, if desired. Such a method comprises a two-electron reduction.

Alternatively, the reduction can be conducted using a living biological system (in the presence of an electron transfer agent) as the reducing agent. Thus, one may use a microorganism that has reducing enzymes, or a suitable extract thereof. For example, the reduction can be accomplished using a culture of *E. coli* as the reducing agent. Any suitable chemical reducing agent can also be employed. By suitable reducing agent is meant one that accomplishes the desired reduction of the Te(IV) derivative without also causing an undesired side reaction. As an example of a suitable chemical reductant, one may cite hypophosphoric acid sodium bisulfite, sodium dithiosulfate, sodium ascorbate, the analogous compounds of other alkali metals, e.g., potassium, and the like.

In general, the reductant is employed in about stoichiometric amounts; however, somewhat greater and lesser amounts can be used, if desired. The reduction is preferably conducted at using mild conditions. In general, process temperatures, pressures, and times, such as described above for the halogenation step, can be employed.

The process of this invention is exemplified by the following illustrative but non-limiting examples. In the examples, the mixtures of dyes that are employed were obtained by synthesis methods such as those illustrated by equations (1) and (2).

EXAMPLE 1

Separation of Dye 1 (an unsymmetrical tellurapyrylium dye from two symmetrical analogs, Dye 2 and Dye 3

In the following formulas, "t-Bu" signifies tert-butyl group:

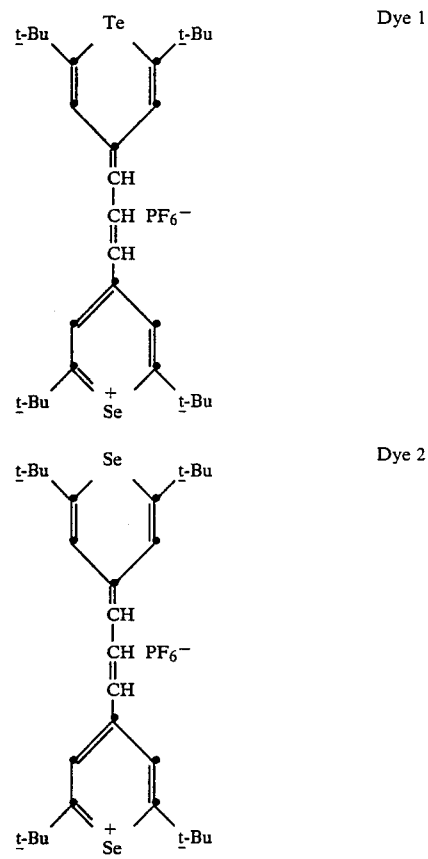

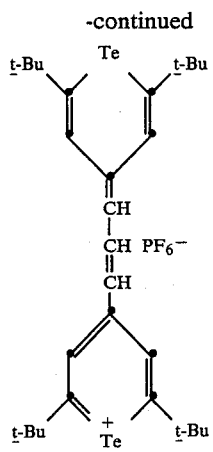

Dye 3

A mixture containing 92% Dye 1, 7% Dye 2, and 11% Dye 3 (0.37 g, 0.50 mmol) was dissolved in 10 mL of dichloromethane. Bromine (0.09 g., 0.55 mmol) in 1 mL of dichloromethane was added via syringe to give a magenta-colored solution. After addition was complete, the reaction mixture was slowly diluted with 10 mL of ether. The resulting mixture was chilled precipitating dark red crystals of Dye 4 which were collected by filtration and dried to give 0.32 g (71%) of material, mP 188°–190° C.:

$^1$H NMR (CD$_3$CN) δ8.65 (d×d, 1 H, J=12, 15 Hz), 8.52 (s, 2H), 7.22 (d, 1 H, J=15 Hz), 7.07 (s, 1 H), 7.01 (d, 1 H, J=12 Hz), 6.56 (s, 1 H), 1.66 (s, 27 1.57 (s, 9 H); λ$_{max}$ (log ε) 546 nm (4.76) in CH$_2$Cl$_2$.

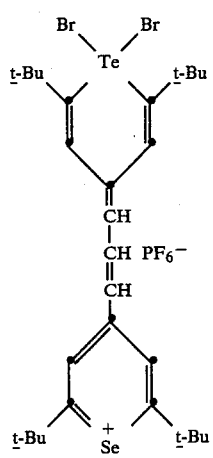

Dye 4

Dye 4 (0.180 g, 0.20 mmol) was dissolved in 5 mL of dichloromethane and 5 mL of methanol. Sodium bisulfite (0.050 g, 0.50 mmol) in 5 mL of water was added. The resulting mixture was stirred for 5 minutes at ambient temperature. The reaction mixture was poured into 20 mL of water. The product was extracted with dichloromethane (2×25 mL). The combined organic extracts were dried over sodium sulfate and concentrated. The residue was recrystallized from 1 mL of acetonitrile and 20 mL of ether to give 0.142 g (96%) of Dye 1 containing less than 1% of Dye 2 and Dye 3 on the basis of $^1$H NMR spectroscopy.

EXAMPLE 2

Separation of Dye 5, from symmetrical analog, Dye 6

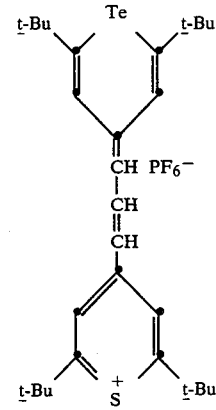

Dye 5

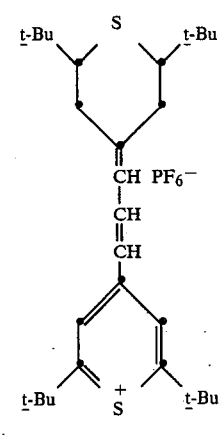

Dye 6

A mixture containing 88% of Dye 1 and 12% of Dye 5 (0.70 g, 1.0 mmol) was dissolved in 20 mL of dichloromethane. Bromine (0.20 g, 1.2 mmol) in 1 mL of dichloromethane was added dropwise giving a red colored solution. After addition was complete, the reaction mixture was stirred for 5 minutes at ambient temperature and was then diluted with 25 mL of ether. Chilling the resulting solution precipitated bright orange crystals of Dye 7 which were collected by filtration and dried to give 0.59 g (78%) of material, mp 190.5°–194.0° C.:

$^1$H NMR (CD$_2$Cl$_2$) δ8.48 (s, 2 H), 8.43 (d×d, 1 H, J=12, 15 Hz), 7.28 (d, 1 H, J=15 Hz), 6.95 (s, 1 H), 6.93 (d, 1 H, J−12 Hz), 6.39 (s, 1 H), 1.67 (s, 18 H), 1.65 (s, 9 H), 1.60 (s, 1 H); λ$_{max}$ (log ε) 524 nm (4.85) in CH$_2$Cl$_2$.

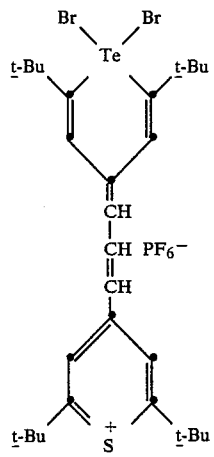

Dye 7

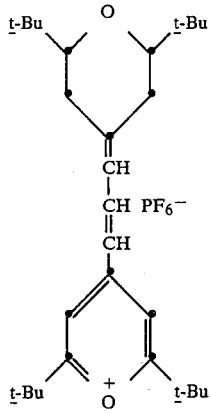

Dye 9 (-continued)

Dye 7 (0.214 g, 0.25 mmol) was dissolved in 5 mL of dichloromethane and 5 mL of methanol. Sodium bisulfite (0.052 g, 0.50 mmol) in 5 mL of water was added. The resulting mixture was stirred for 5 minutes at ambient temperature. The reaction mixture was poured into 50 mL of water, and the products were extracted with dichloromethane (2×25 mL). The combined organic extracts were dried over sodium sulfate and concentrated. The residue was recrystallized from 1 mL of acetonitrile and 25 mL of ether to give yellow-green crystals of Dye 5 (0.141 g, 81% mp 220°-221° C., containing less than 1% of Dye 6 by $^1$H NMR.

The following examples also illustrate the separation of unsymmetrical tellurapyrylium dyes (Dye 8 and Dye 11) from symmetrical analogs thereof.

EXAMPLE 3

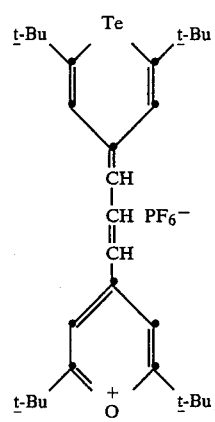

Dye 8

A mixture containing 85% of Dye 8 and 15% of Dye 9 (0.034 g, 0.050 mmol) was dissolved in 1 mL of dichloromethane. Bromine (0.016 g, 0.10 mmol) in 1 mL of dichloromethane was added and the resulting solution was stirred for 5 minutes at ambient temperature. The reaction mixture was diluted with 5 mL of ether precipitating an orange solid. The orange crystals of Dye 10 were collected by filtration and dried to give 0.035 g (92% based on Dye 8) of material, mp 178°-180° C.:

$^1$H NMR (CD$_2$Cl$_2$) $\delta$8.40 (d×d, 1 H, J=12, 15 Hz), 7.73 (s, 2 H), 7.05 (d, 1 H, J=15 Hz), 6.90 (s, 1 H), 6.89 (d, 1 H, J−12 Hz), 6.38 (s, 1 H), 1.65 (s, 9 H), 1.60 (s, 9 H), 1.55 (s, 18 H); $\lambda_{max}$ (log $\epsilon$) 510 nm (4.60) in CH$_2$Cl$_2$.

Dye 10

Dye 10 (0.021 g, 0.025 mmol) was dissolved in 2 mL of dichloromethane and 2 mL of methanol. Sodium bisulfite (0.010 g, 0.10 mmol) in 2 mL of water was added. The resulting mixture was stirred for 10 minutes at ambient temperature. The reaction mixture was poured into 20 mL of water, and the products were extracted with dichloromethane (2×20 mL). The combined organic extracts were dried over sodium sulfate and concentrated. The residue was recrystallized by the addition of 20 mL of ether. Green crystals of Dye 8 (0.014 g, 82%) were collected by filtration. The Dye 8, mp 198°-200° C. contained less than 1% Dye 9 by $^1$H NMR.

EXAMPLE 4

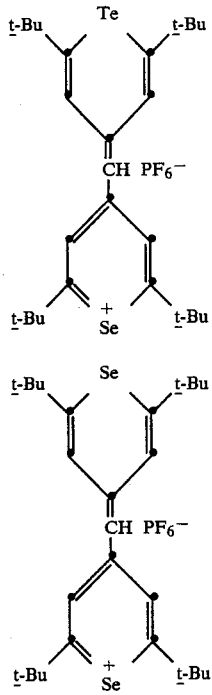

Dye 11

Dye 12

A mixture containing 95% of Dye 11 and 5% of Dye 12 (0.075 g, 0.10 mmol) was dissolved in 10 mL of dichloromethane. Chlorine gas was bubbled into the solution until the blue color faded to bright orange. The reaction mixture was concentrated and the residue was recrystallized from acetonitrile to give 0.063 g (77%) of Dye 13 as a yellow-green solid, mp 202°–206° C.:

$^1$H NMR (CD$_2$Cl$_2$) δ8.23 (s, 2 H), 7.23 (s, 1 H), 6.49 (s, 1 H), 6.43 (s, 1 H), 1.66 (s, 18 H), 1.56 (s, 9 H), 1.50 (s, 9 H); Anal. Calcd. for C$_{27}$H$_{41}$Cl$_2$SeTe.PF$_6$: C, 39.6; H, 5.1. Found: C, 39.9; H, 5.3.

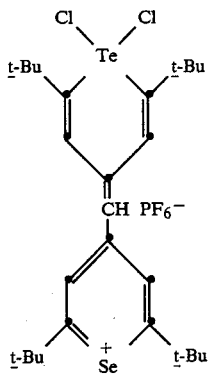

Dye 13

Dye 13 (0.021 g, 0.025 mmol) was dissolved in 2 mL of dichloromethane and 2 mL of methanol. Sodium bisulfite (0.010 g, 0.10 mmol) in 2 mL of water was added. The resulting mixture was stirred for 10 minutes at ambient temperature. The reaction mixture was poured into 20 mL of water, and the products were extracted with dichloromethane (2×20 mL). The combined organic extracts were dried over sodium sulfate and concentrated. The residue was recrystallized by the addition of 20 mL of ether. Green crystals of Dye 11 (0.014 g, 82%) were collected by filtration. The Dye 11, mp 198°–200° C. contained less than 1% Dye 12 by $^1$H NMR.

EXAMPLE 5

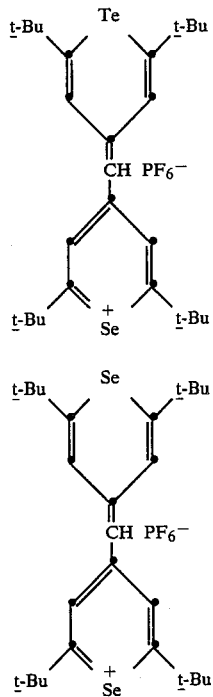

Dye 11

Dye 12

A mixture containing 95% of Dye 11 and 5% of Dye 12 (0.072 g, 1.0 mmol) was dissolved in 15 mL of dichloromethane. Bromine (20 g, 1.25 mmol) in 1 mL of dichloromethane was added. The resulting mixture was stirred for 5 minutes at ambient temperature and was concentrated. The residue was recrystallized from acetonitrile to give 0.53 g (60%) of Dye 14, mp 201°–205° C.:

$^1$H NMR (CD$_2$Cl$_2$) δ8.22 (s, 2 H), 7.23 (s, 1 H), 6.49 (s, 1 H), 6.46 (s, 1 H), 1.64 (s, 18 H), 1.57 (s, 9 H), 1.53 (s, 9 H); Anal. Calcd. for C$_{27}$H$_{41}$Br$_2$SeTe.PF$_6$: C, 35.8; H, 4.6. Found: C, 36.1; H, 4.7.

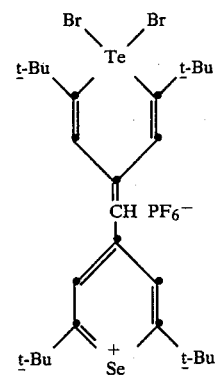

Dye 14

Dye 14 (0.088 g, 0.10 mmol) was dissolved in 2 mL of dichloromethane and 2 mL of methanol. Sodium ascorbate (0.080 g) in 2 mL of water was added. The resulting mixture was stirred for approximately 15 minutes at ambient temperature. The reaction mixture was poured into 20 mL of water, and the products were extracted with dichloromethane (2×20 mL). The combined organic extracts were dried over sodium sulfate and concentrated. The residue was recrystallized from 0.5 mL of acetonitrile and 10 mL of ether to give 0.065 g (90%) of Dye 11, mp 223°–227° C., containing less than 1% Dye 12 by $^1$H NMR.

As can be seen by the examples, the process of this invention can be used to remove symmetrical analogs from unsymmetrical tellurapyrylium dyes such that the content of symmetrical analogs is reduced to less than 1%, as shown by NMR. A preferred embodiment of this invention comprises lowering the analog content of a UTPD to this level.

The procedures illustrated can be modified to employ other reducing agents and methods such as those discussed above. Likewise, the process illustrated by the examples can be modified to use other solvents and reaction conditions such as those discussed above.

Following the procedure illustrated by the above examples, one may upgrade the purity of other umsymmetrical tellurapyrylium dyes, such as those within Formula (I), by separating them from analogs thereof within Formula (II).

The process of this invention can be extended to the use of non-halogen mild oxidants instead of the halogen-type oxidants disclosed above. For example, hydrogen peroxide and similar oxidants can be employed. However, the use of halogens as oxidants is preferred, since the separation procedure comprising their use gives better results.

The invention has been defined and illustrated above with particular reference to preferred embodiments thereof. A skilled practitioner, familiar with the above description, can make many modifications and substitutions without departing from the scope and spirit of the following claims.

I claim:

1. A process for upgrading the purity of an unsymmetrical tellurapyrylium dye, said dye having an tellurapyrylium nucleus at one end of a methine-type bridge and a pyranyl, thiapyranyl, or selenapyranyl nucleus at the other end of said bridge, by separating said dye from a symmetrical pyrylium, thiapyrylium, selenapyrylium, or tellurapyrylium analog of said dye;

said dye and said analog comprising a mixture wherein said dye is at least about 50 mole percent or greater, said process comprising contacting a solution of said mixture of said dye and said analog in an inert organic solvent with a halogen, whereby a tellurium(IV) derivative of said dye is formed, precipitating said derivative from the reaction mixture thereby produced by fractional crystallization thereby leaving impurities in solution, and reducing said derivative with a reducing agent to reform said dye.

2. Process of claim 1 whereby Dye 1 is separated from a mixture of Dye 1, Dye 2 and Dye 3,

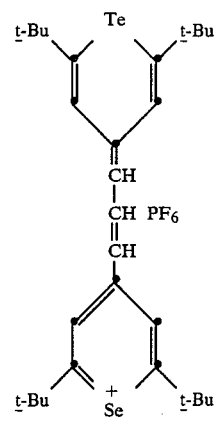
Dye 1

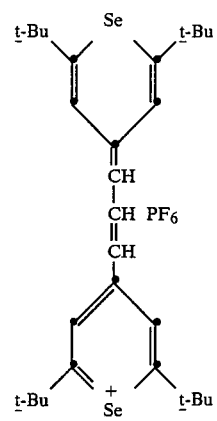
Dye 2

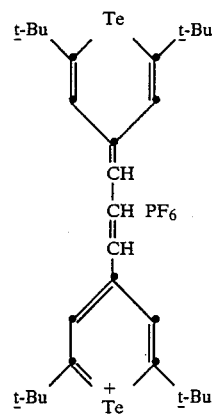
Dye 3 said process comprising (a) contacting said mixture and bromine in dichloromethane to produce Dye 4,

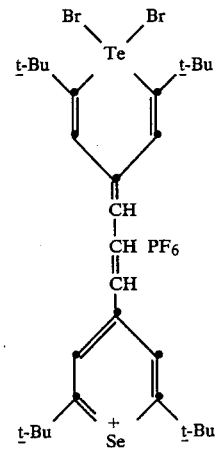

Dye 4

(b) precipitating Dye 4 by diluting with ether and chilling, and (c) subsequently reacting Dye 4 with sodium bisulfite to regenerate Dye 1.

3. Process of claim 1 wherein said solvent is selected from lower alcohols, acetonitrile and dichloromethane.

4. Process of claim 1 wherein said fractional crystallization is conducted by adding a second solvent to said reaction mixture to reduce the solubility of said derivative.

5. Process of claim 1 wherein said second solvent is diethyl ether.

6. A process according to claim 3 wherein said mixture and said halogen are dissolved in dichloromethane.

7. A process according to claim 1 wherein said halogen is selected from the class consisting of chlorine and bromine.

8. A process according to claim 7 wherein said halogen is bromine.

9. A process according to claim 3 wherein said fractional crystallization is conducted by chilling the solution obtained by contacting said mixture and halogen in said organic solvent.

10. A process according to claim 9 wherein said derivative is separated from the liquid phase produced as a by-product by said fractional crystallization, and subsequently redissolved in an inert organic solvent prior to contacting said derivative with said reducing agent.

11. A process for upgrading the purity of an unsymmetrical tellurapyrylium dye, said dye having a tellurapyrylium nucleus at one end of a methine-type bridge and a pyranyl, thiapyranyl, or selenapyranyl nucleus at the other end of said bridge, by separating said dye from a symmetrical pyrylium, thiapyrylium, or selenapyrylium analog of said dye;

said process comprising contacting a solution of said dye and said analog in an inert organic solvent with a halogen, whereby a tellurium(IV) derivative of said dye is formed, precipitating said derivative from the reaction mixture thereby produced by fractional crystallization thereby leaving impurities in solution, and reducing said derivative with a reducing agent to reform said dye.

12. Process for separating Dye 5 from a mixture of Dye 5 and Dye 6,

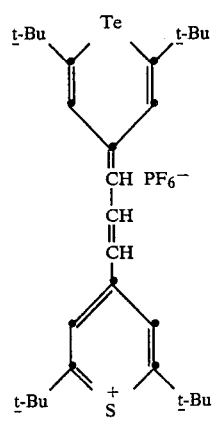

Dye 5

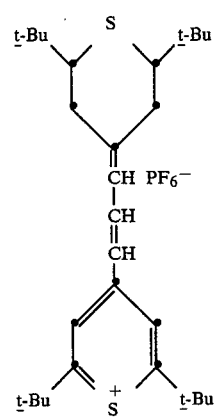

Dye 6 said process comprising (a) contacting said mixture and bromine in dichloromethane to form Dye 7,

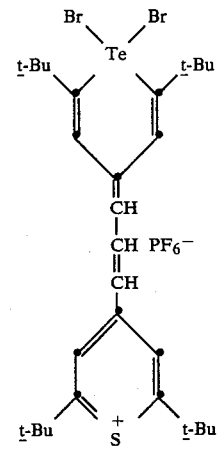

Dye 7

(b) removing Dye 7 from the reaction mixture thereby produced by chilling said mixture, and (c) subsequently reacting Dye 7 with sodium bisulfite to regenerate Dye 5.

13. Process of separating Dye 8 from a mixture of Dye 8 and Dye 9,

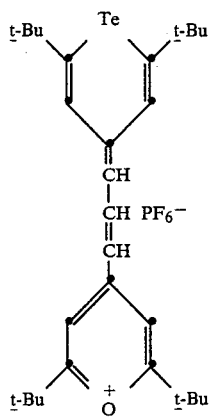

Dye 8

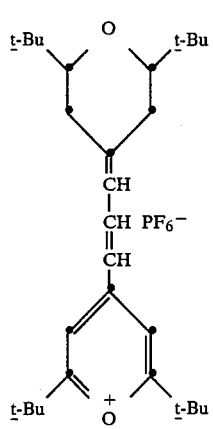

Dye 9 said process comprising (a) contacting said mixture with bromine in dichloromethane to prepare Dye 10,

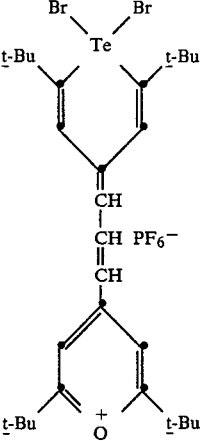

Dye 10

(b) separating Dye 10 from the reaction mixture thereby produced by precipitation with ether, and (c) subsequently reacting Dye 10 with sodium bisulfite to regenerate Dye 8.

14. Process of separating Dye 11 from a mixture of Dye 11 and Dye 12,

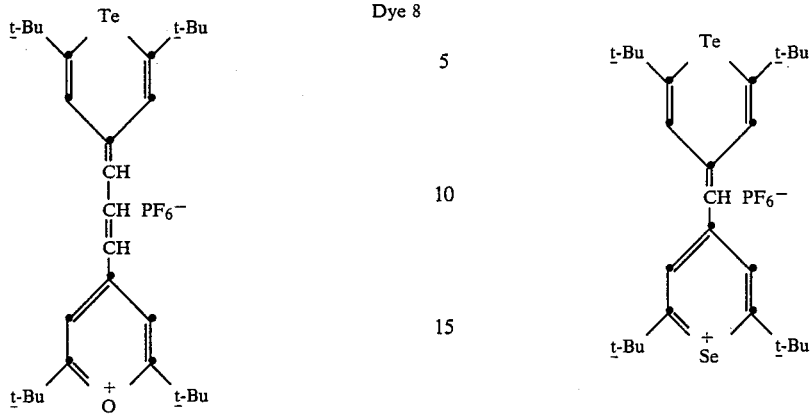

Dye 11

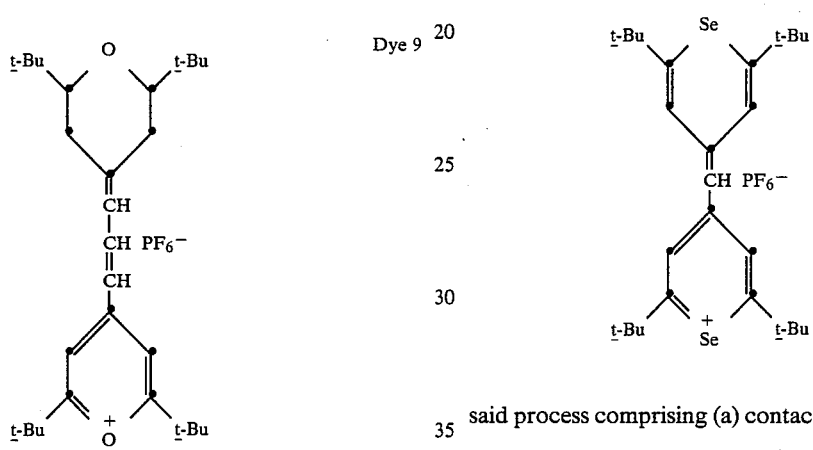

Dye 12 said process comprising (a) contacting said mixture with chlorine in dichloromethane, to prepare Dye 13,

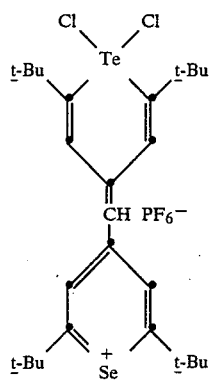

Dye 13

(b) separating Dye 13 from the reaction mixture thereby produced by concentrating said residue and recrystallizing Dye 13 from acetonitrile, and (c) subsequently reacting Dye 13 with sodium bisulfite to regenerate Dye 11.

15. Process of separating Dye 11 from a mixture of Dye 11 and Dye 12,

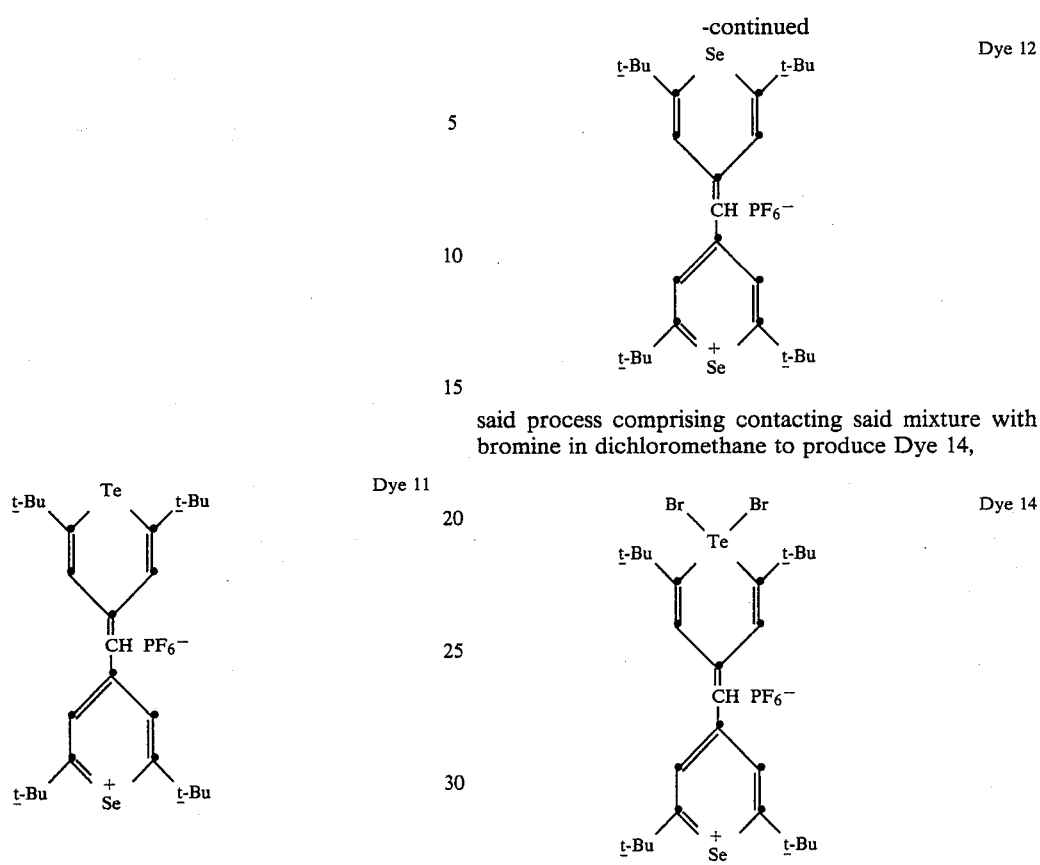
said process comprising contacting said mixture with bromine in dichloromethane to produce Dye 14,
(b) separating Dye 14 from the reaction mixture thereby produced by concentrating said reaction mixture, and recrystallizing Dye 14 in acetonitrile, and (c) subsequently reacting Dye 14 with sodium ascorbate to regenerate Dye 11.
* * * * *